(12) United States Patent
Hajizadeh et al.

(10) Patent No.: US 6,180,417 B1
(45) Date of Patent: Jan. 30, 2001

(54) IMMUNOCHROMATOGRAPHIC ASSAY

(75) Inventors: Kiamars Hajizadeh; Dayaweera Wijesuriya, both of Granger, IN (US)

(73) Assignee: Bayer Corporation, Elkhart, IN (US)

( * ) Notice: Under 35 U.S.C. 154(b), the term of this patent shall be extended for 0 days.

(21) Appl. No.: 09/295,575

(22) Filed: Apr. 22, 1999

(51) Int. Cl.[7] .................................................. G01N 33/533
(52) U.S. Cl. .............................. 436/518; 422/56; 422/57; 422/58; 422/60; 422/61; 435/7.1; 435/7.92; 435/7.93; 435/7.94; 435/287.7; 435/287.8; 435/287.9; 435/288.3; 435/288.4; 435/288.5; 435/970; 436/541; 436/161; 436/810
(58) Field of Search .................................. 422/56, 57, 58, 422/60, 61; 435/7.1, 7.92, 7.93, 7.94, 287.7, 287.8, 287.9, 288.3, 288.4, 288.5, 970; 436/518, 541, 161, 810

(56) References Cited

U.S. PATENT DOCUMENTS 4,956,302 * 9/1990 Gordon et al. .
4,978,503 * 12/1990 Shanks et al. .
5,234,813 * 8/1993 McGeehan et al. .
5,939,331 * 8/1999 Burd et al. .

FOREIGN PATENT DOCUMENTS 0291194 2/1994 (EP) .

* cited by examiner

Primary Examiner—Long V. Le
Assistant Examiner—Bao-Thuy L. Nguyen
(74) Attorney, Agent, or Firm—Jerome L. Jeffers

(57) ABSTRACT

Disclosed is a device and method for carrying out an assay for an analyte in a fluid test sample by immunochromatography. The device involves a strip having a non-porous receiving member of a hydrophobic material in direct fluid communication with a reagent region of an absorbent material through which the fluid test sample can flow by capillarity. By applying the fluid test sample to the non-porous hydrophobic receiving member rather than directly to the absorbent material the reliability of the assay is enhanced.

14 Claims, 1 Drawing Sheet

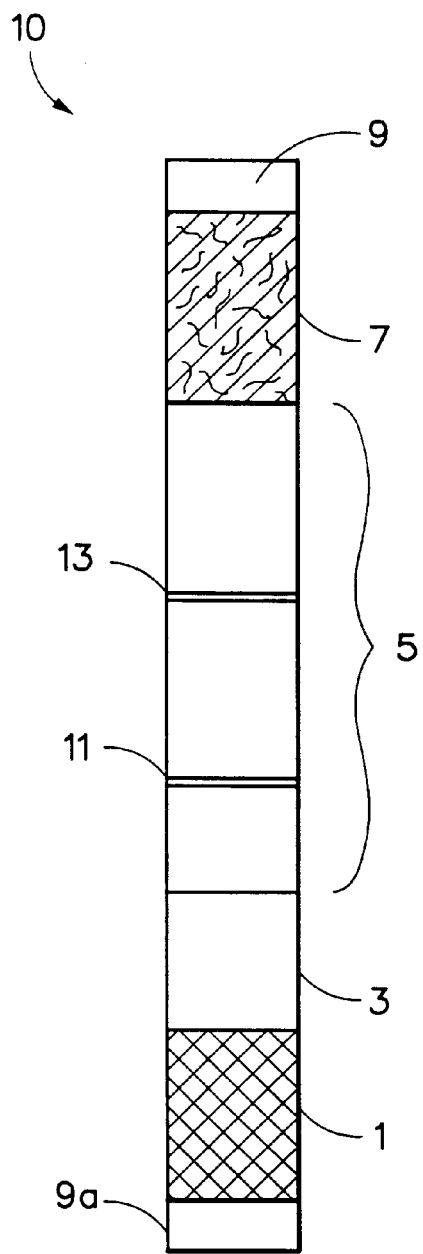
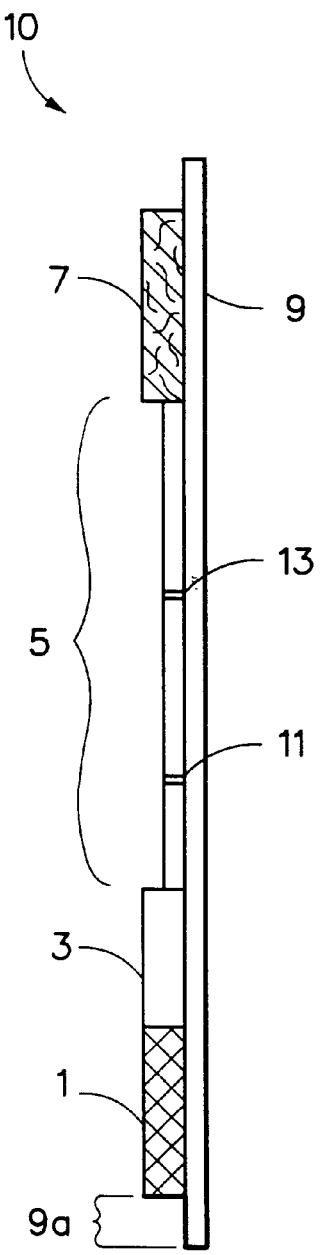
FIG. 1A
FIG. 1B

IMMUNOCHROMATOGRAPHIC ASSAY

BACKGROUND OF THE INVENTION

Immunochromatographic strip formats have become increasingly popular for qualitative and semiquantitative assays which use visual detection schemes. This type of assay involves the application of a liquid test sample suspected of containing the analyte to be detected to an application zone of an immunochromatographic test strip. The strip is comprised of a matrix material through which the test fluid and analyte suspended or dissolved therein can flow by capillarity from the application zone to a capture zone where a detectable signal, or the absence of such, reveals the presence of the analyte. Typically, the strip will include means for immunospecifically binding the analyte to be detected with its specific binding partner which bears the detectable label. The label may be one that is visible to the naked eye such as colloidal metal particles or colored latex, an enzyme that forms a visible signal when contacted with a suitable substrate or one that is detectable only with the use of an instrument such as a chemilumenescent or radio active label. In one such scheme, the strip contains an enzyme labeled, mobile binding partner for the analyte which is in a sample application zone. If analyte is present in the test sample, it will combine with its labeled binding partner to form a complex which will flow along the strip to a detection zone which contains a substrate for the enzyme label which is capable of providing a colored response in the presence of the enzyme. The strip may contain a zone in which analyte is immobilized, so that labeled binding partner which does not combine with analyte, due to the absence of analyte in the sample, will be captured and thereby inhibited from reaching the detection zone. There have been published various modifications of this technique, all of which involve some competitive specific binding system in which the presence or absence of analyte in the test sample is determined by the detection or lack thereof of labeled binding partner in the capture zone.

An alternative to the above described immunometric assay which detects the free labeled antibody is the so called sandwich format in which the capture zone contains immobilized antibodies against an epitope of the analyte to which the labeled antibody is specific. In this format, there is formed a sandwich of the analyte between the immobilized and labeled antibodies to provide the detectable signal in the capture zone.

Not all of the schemes for immunochromatography rely on an enzyme labeled binding partner/enzyme substrate for providing the signal for detection of the analyte. In U.S. Pat. No. 4,806,311 there is disclosed a multizone test device for the specific binding assay determination of an analyte and an immobilized binding partner for the analyte together with a capture zone for receiving labeled reagent which migrates thereto from the reagent zone. The capture zone contains an immobilized form of a binding substance for the labeled reagent. The labeled reagent bears a chemical group having a detectable physical property which is detectable on the basis of such physical property, so that it does not require a chemical reaction with another substance in order to be detected. U.S. Pat. No. 4,703,017 describes the use of visible particulate labels for the receptor. Various particulate labels such as gold sol particles and visible dye containing liposomes are mentioned.

European Patent 0 291 194 discloses an immunochromatographic strip of the type presently under consideration. In describing the receiving member this patent states that it can be made from any bibulous, porous or fibrous material including porous plastics such as polypropylene, polyethylene, polyvinylidine fluoride, ethylene vinyl acetate, acrylonitrile or polytetrafluoro-ethylene. While the patentees recognize that some of these materials are hydrophobic, they suggest pretreating the material with a surfactant to reduce the inherent hydrophobicity. The prior art strips typically employ a porous receiving member to absorb the test fluid rapidly so that the strip will quickly become fully wetted when dipped into a test fluid such as urine. However, this wettability of the test strip can become problematical when sample volume is critical such as when the fluid test sample is whole blood obtained from a finger prick. In the case of test strips having a hydrophilic sample receiving member, there is generally a need for higher sample volumes since the hydrophilic member will take up some liquid, depending on its porosity, before sample can reach the next section of the strip. One way to minimize sample volume is by reducing the dimensions of or by miniaturizing the test strip. This approach may not always be suitable due to certain constraints on the dimensions of an encasing cassette for the strip or on an instrument such as a reflectance spectrometer used to read the strip which may not be sufficiently sensitive in some cases.

It would be desirable and it is an object of the present invention to provide an immunochromatography strip of the type described above in which the fluid test sample is drawn from the strip's receiving member to its reagent portion with reduced sample volume.

SUMMARY OF THE INVENTION

The present invention involves an assay for determining the presence or concentration of an analyte in a fluid test sample by the application of the fluid to the receiving member of an immunochromatographic test strip. The strip's receiving member is in fluid communication with the reagent portion of the strip which includes at least an absorbent material through which the test fluid can flow and which contains a mobile, labeled specific binding partner for the analyte wherein the concentration of the analyte in the fluid test sample is determined by measuring the amount of labeled specific binding partner which is captured by a capture mechanism in the reagent portion of the strip. The invention disclosed herein is an improvement to this type of assay which involves the use of a test strip in which the receiving member is made of a nonporous, hydrophobic material.

By providing a hydrophobic platform as a sample receiving pad, a more efficient and uniform release of the labeled conjugate can be achieved. The precision of reflectance values from detection and control regions of the device are also improved. The hydrophobic nature of the pad, which prevents sample absorption, permits the use of smaller volumes of the test sample as opposed to a conventional immuno test strip which uses an absorbant pad for wicking the test sample.

BRIEF DESCRIPTION OF THE DRAWINGS

FIGS. 1A and 1B represent front and side views respectively of a strip device useful in the present invention.

DESCRIPTION OF THE INVENTION

Referring to FIGS. 1A (top view) and 1B (side view), the device of the present invention comprises a backing member 9 which is made of a hydrophobic, non-porous material such as polystyrene, polyethylene, polypropylene or other nonbibulous hydrophobic material upon which are placed the absorbent portions of the device. The nonporous sample application zone is a solid, impervious hydrophobic material or a solid impervious surface treated to give it hydrophobic properties. The use of such an impervious hydrophobic surface prevents fluid sample applied to it from spreading excessively thereby maximizing the total sample which is available to the system. As a result, sample volume can be minimized in situations, such as a finger stick, where a small sample volume is used either by preference or necessity. In this preferred embodiment, a portion 9a of the hydrophobic, non-porous material is left uncovered by absorbent material to provide the sample application zone. Alternatively, a piece of hydrophobic, non-porous material can be applied to the backing member to serve as the hydrophobic, non-porous material for the sample application zone 9a in which case the backing member 9 can be made of materials other than those which are hydrophobic and non-porous. The hydrophobic, non-porous sample application zone need not be limited to those materials mentioned above; other materials such as polytetrafluoro ethylene and materials that are surface treated with hydrophobic materials such as perfluoro ethylene and silanizing agents, can be used with equivalent results. The terms hydrophobic and non-porous, for purposes of this description, are intended to mean that the materials are water repellent and do not absorb any of the liquid test sample. The hydrophobic surface does not absorb fluid test sample which is of an aqueous nature and thereby yields a maximum sample volume for transport across the reagent region. This is especially desirable when the sample volume is limited. Moving upstream in the direction of fluid test sample flow is conjugate pad 1 which is in direct fluid communication with the hydrophobic, non-porous application zone 9a. The conjugate pad is typically made of an absorbent, porous material such as glass fiber, polyester or other woven or non-woven synthetic material through which the fluid test sample can flow and contains mobile conjugate of one or more labeled specific binding partners. The specific binding partner, typically an antibody, can be labeled with an enzyme, fluorofor, radio active isotope or, preferably, a direct particulate label such as gold sol or colored latex particles. When the fluid test sample is applied to the hydrophobic, non-porous application zone in direct physical contact with the conjugate pad it is absorbed into the conjugate pad where it contacts the labeled specific binding partner and carries it further up the device towards bridging pad 3. Fluid transfer between the application zone and reagent zone (in this case the conjugate pad) is improved over that observed when the application zone is made from other than a hydrophobic, non-porous material because the interface between the application pad and the conjugate pad is eliminated. Irregularities through this interface can cause non-uniform flow patterns leading to test result variations. This configuration also requires a smaller sample volume. The hydrophobic properties of the sample application zone prevents the sample from spreading widely, so that it can flow through the conjugate pad which is the least resistant path.

Upstream on the device from the conjugate pad is the bridging pad 3 which serves the purpose of providing a mixing port to ensure the uniform mixture of reactive reagents reaching the detection zones. It also serves to prevent excess red blood cells which may not have been fixed in the prior zone from entering the detection zones and can be made of a material such as polyester or glass fiber. Downstream from the bridging pad 3 is the read region 5 which can be made of a material such as nitrocellulose, cellulose or polyethylensulfonate through which the fluid test sample carrying the reagents (labeled specific binding partner and analyte with which the specific binding partner has reacted) can flow and to which the capture means will adhere. Thus, detection zone 11 can have immobilized thereon either analyte (or a binding analog thereof) in the case of a competitive immunoassay in which labeled binding partner specific for the analyte is competed for by analyte in the test sample is immobilized in the detection zone. Alternatively, there can be immobilized in the detection zone a specific binding partner which is specific for an epitope of the analyte different to that epitope to which the labeled specific binding partner is specific, so that a labeled specific binding partner-analyte-immobilized specific binding partner sandwich will form in the presence of analyte. The competition (binding inhibition) and sandwich formation could take place in the conjugate pad in which case the detection zone would serve as a universal capture zone.

The read region 5 can also contain a control zone 13 wherein labeled antibody is captured to demonstrate to the user that the assay has been carried out properly. Typically, the control zone has immobilized thereon binding partners which are specific to the labeled binding partner such as anti-mouse IgG when the labeled specific binding partner is a murine antibody. The control binding partner can be attached to a separate label such as latex or onto the same label as that used for analyte detection. Finally, there is absorbant pad 7 whose function is to act as a sink for removing excess unreacted reagents and to serve as a pump for efficient capillary flow through the test strip. The absorbent pad can be derived from absorbent materials such as cellulose, desiccant treated cellulose and surfactant treated porous polymers.

The only two elements which are critical to the operability of the present invention are the solid support and reagent portion of the strip in fluid communication with the solid support. When not covered by the reagent portion the solid support serves as the strip device's receiving member. Thus, in this embodiment, the solid support 9 also serves as the receiving member 9a when it is constructed from a non-porous, hydrophobic material. Alternatively, a separate receiving member can be applied to the solid support and mated closely with the reagent portion of the strip so that it is in fluid communication with the reagent portion. While the reagent portion of the strip is depicted as being comprised of separate pieces in the drawings, it is to be understood that this is the preferred embodiment of the invention and that a single strip could be used provided that it is constructed using a material through which the fluid test sample can flow and which is capable of maintaining the appropriate reagents (mobile labeled binding partner specific for analyte in the test sample and an immobilized capture mechanism for the analyte or labeled binding partner). This could be accomplished by affixing a single pad of absorbent material, such as nitrocellulose, to the backing member 9 which would contain the mobile conjugate and bear the detection site 11 and control site 13. In general, the reagent zone of the device is made of an absorbent material such as paper or other membrane that has been treated with a respective reagent which is associated with a particular assay to be performed. The immunoassay components can be applied to a sheet of the absorbent material which is then cut into strips of the appropriate size and adhered to the backing material in such a manner that provides direct physical contact between the hydrophobic, non-porous application zone of the device and its reagent zone.

Although the device of the present invention is suitable for conducting immunoassays using various body fluids such as urine, saliva, sweat or mucous it is particularly suitable for assays in which blood is the test fluid. This is the case because of the desire for a test which requires only a small sample volume when the blood is collected by means such as a finger stick.

The device can be used as is or enclosed in a casing such as that described in previously mentioned European Patent 0 291 194. In either embodiment the device is used by applying a sample of the fluid test sample to the application zone either directly or through an application port in the casing. By applying the fluid sample to the hydrophobic non-porous application zone in partial contact with the absorbent reagent portion of the device, the sample is sorbed into and through the reagent zone more efficiently than if it were applied directly to the absorbent reagent material. This is the case because by applying sample to the hydrophobic sample application zone in contact with the absorbent portion of the device the liquid moves upstream towards the detection zones which leads to a more uniform release of reagents. Conversely, if the sample is directly applied to the reagent zone, it reaches the detection area. This tends to slow the release of reagents. This leads to longer test times and considerable unreleased reagent being left behind in the absorbant reagent containing material resulting in a lower response to analyte contained in the test sample.

Many clinically significant target analytes are present in body fluids and can be assayed using the device and method of the present invention. Thus, in urine, analytes such as deoxypyrodinoline, human serum albumin, drugs of abuse, protein markers such as prostate specific antigen, kidney disease proteins such as lactate dehydrogenate, N-acetyl-β-D-glucosamine, pregnancy or fertility associated hormones such as human chorinic gonadotropin and markers of urinary tract infection can be assayed. The determination of blood borne analytes such as therapeutic drugs, hormones, cancer markers such as prostate specific antigen, cardiac markers (Troponin I, Troponin T, CKMB) and α-fetoprotein is particularly suited to the present invention.

While the means for detecting the signal(s) from the reagent zone of the present device will depend on the type of detectable label attached to the labeled binding partner, the use of a reflectance spectrometer is typical when the label's detectable physical property is the reflectance of light at a predetermined wavelength. In a preferred embodiment of using the device, there is provided a reflectance meter with means for moving the test strip or moving the meter's detector element relative to each other such as by the use of a specimen table for the strip which can be moved laterally under the readhead of the detector. The reflectance from the detection zone of the read region can be read to obtain the concentration of the analyte in the fluid sample and then the device can be shifted on the specimen table for reading the reflectance of the control zone.

The method of practicing the present invention is more fully illustrated by the following example:

EXAMPLE I

Test strips were prepared according to the design of FIGS. 1A and 1B in a clam shell laminator. To a polystyrene backing (5.6 cm×0.765 cm) were applied a nitrocellulose strip (2.5 cm long) and upstream from this strip were applied a 0.7 cm long bridging pad made of prelaminated glass fiber (Whatman F075-075) and a 0.9 cm long conjugate pad of loosely consolidated amorphous glass fiber which contained anti-PSA monoclonal antibody labeled with fluoroscein isothiocyanate (FITC). These sections were applied so as to leave 0.4 cm of the polystyrene backing exposed to serve as the hydrophobic platform for application of the liquid test sample. Downstream from the nitrocellulose strip there was applied a 1.0 cm long piece of desiccant impregnated absorbent cellulose paper as absorbant pad.

The nitrocellulose strip was provided with test and control lines which were prepared by applying 3.0 mg/mL of monoclonal mouse anti-FITC as test line and 3.75 mg/mL glucose oxidase (GO) as control line. (as test and control line proteins) onto the strip using an IVEK striper. The conjugate pad was impregnated with a mixture of 125 μg/ml anti-GO-latex, 350 mg/ml anti-PSA-latex, 5 μg/ml FITC-anti-PSA, 3.16 mg/mL chremophore, 0.23% casein, 20.9 mg/mL HEPES, 23.3 mg/mL maltose, 9.32 mg/mL BSA, 1.45 mg/mL goat IgG and 1.1 mg/mL potato lectin and dried using an Overly dryer at zones of 70, 60 and 50° C. at a speed of 120 cm/min.

The device was tested by applying 75 μL of whole blood spiked with complex PSA calibrator to the test strip by pipetting it onto the polystyrene hydrophobic platform, the conjugate pad or a porous buffer pad placed in front of the conjugate pad. The blood sample was sorbed into the conjugate pad and through the reaction zones of the test strip which served to separate red cells from the whole blood as the blood migrated through the various zones of the strip. The bridge pad serves to ensure efficient mixing of the conjugate and blood sample and helps to prevent red blood cells from entering the nitrocellulose area where they could obscure the signal from the test and control zones. The developed strips were read by determining the reflectance from the test zone at 625 nm using a CLINITEK® reflectance meter 10 minutes after application of the blood sample.

Three formats were compared with respect to fluid run characteristics and overall test performance. In format "A" sample was applied to the middle of the polystyrene platform at 1–2 mm from the conjugate pad, so that the test fluid touched the pad. In format "B" the blood sample was applied to the middle of the poruos conjugate pad. In format "C" the sample was applied to a porous buffer pad made of glass fiber placed in front of the conjugate pad. This is the most common format used in immunochromatography strips. Table 1 illustrates the control and test line intensity and the error associated with each of the three formats. The test and control band reflectance values (% R) were measured in triplicate using a CLINITEK® reflectance meter. The signal STDs and CVs were calculated using background subtracted peak reflectance values (n=3) to determine error in each case.

TABLE 1

|  |  | Control Line | | | Test Line | | |
| --- | --- | --- | --- | --- | --- | --- | --- |
|  | PSA, ng/ml | % R | STD | CV | % R | STD | CV |
| Format A | 0 | 5.6 | 0.67 | 12.1 | 0 | 0 | 0 |
|  | 4 | 5.8 | 0.55 | 9.48 | 7.02 | 0.52 | 7.42 |
|  | 10 | 5.3 | 0.52 | 9.93 | 13.3 | 0.26 | 1.94 |
| Format B | 0 | 0 | 0 | 0 | 0.4 | 0.81 | 200 |
|  | 4 | 0 | 0 | 0 | 3.55 | 0.83 | 23.5 |
|  | 10 | 0 | 0 | 0 | 7.04 | 0.73 | 10.4 |
| Format C | 0 | 4.7 | 1.68 | 35.8 | 0 | 0 | 0 |
|  | 4 | 5.8 | 3.88 | 67.5 | 4.43 | 1.33 | 29.9 |
|  | 10 | 7.4 | 1.91 | 25.9 | 9.91 | 1.71 | 17.2 |

From Table 1 it can be determined that format A, which involves the nonporous hydrophobic platform of the present invention, shows significant superiority in terms of improved precision (lower CV) and reproducible formation of the control line. Format B does not form a control line and format C gives a high degree of imprecision (high CV) for the control line.

What is claimed is:

1. An assay for determining the presence or concentration of an analyte in a fluid test sample which comprises:
    a) providing an immunochromatographic test strip having a non-porous receiving member of a hydrophobic material in direct fluid communication with a reagent region of an absorbant material through which the fluid test sample and reagents carried therein can flow by capillarity and which reagent region contains a detection site for detecting the presence or concentration of the analyte,
    b) applying the fluid test sample to the receiving member, so that a portion of the fluid test sample is in direct contact with the absorbant material of the reagent region of the immunochromatographic test strip, and
    determining the presence or concentration of the analyte in the fluid test sample by correlating a detectable response in the reagent region with such presence or concentration.

2. The assay of claim 1 wherein the reagent region contains labeled specific binding partner for the analyte which are free to flow through the reagent region with the fluid test sample and the reagent region also contains an immobilized binder capable of binding the specific binding partner.

3. The assay of claim 2 wherein the labeled specific binding partner is an antibody which is specific for one epitope of the analyte and the immobilized binder is an antibody which is specific for a different epitope of the analyte.

4. The assay of claim 1 wherein the fluid test sample comprises blood.

5. The assay of claim 1 wherein the non-porous receiving member comprises polyethylene, polypropylene, polytetrafluoro-ethylene, or a material whose surface has been treated with a hydrophobic material.

6. The assay of claim 5 wherein the hydrophobic material is perfluoro ethylene or a silanizing agent.

7. The assay of claim 1 wherein the immunochromatographic test strip has a conjugate pad between the receiving member and the reagent region which conjugate pad contains one or more labeled specific binding partners at least one of which is specific for at least one epitope of the analyte.

8. The assay of claim 1 wherein there is a bridging pad which provides a zone for mixing the fluid test sample and labeled specific binding partner before they reach the reagent region of the immunochromatograpic test strip.

9. The assay of claim 8 wherein the bridging pad is comprised of polyester or glass fiber.

10. The assay of claim 1 wherein the immunochromatographic test strip has a separate read region downstream from the bridging pad which region has at least one zone in which there are immobilized immunoreactants for at least one epitope of the analyte or a binding analog thereof.

11. The assay of claim 10 wherein the read region has a separate zone in which there is immobilized an immunoreactant for the labeled specific binding partner in the reagent region.

12. The assay of claim 11 wherein the immunochromatographic test strip has an absorbent pad downstream from and in contact with the read region which serves to draw the fluid test sample through the strip by capillarity.

13. The assay of claim 10 wherein the read region is comprised of cellulose or polyethylenesulfonate.

14. A test strip for the determination of an analyte in a fluid test sample which comprises a base member of a non-porous, hydrophobic material which base member has on its surface a pad of absorbent material through which the fluid test sample and reagents carried therein can flow wherein the base member has sufficient surface area which is not covered by the pad of absorbent material for application of the fluid test sample directly to the base member.

* * * * *